(12) United States Patent
Kobayashi

(10) Patent No.: US 10,047,037 B2
(45) Date of Patent: Aug. 14, 2018

(54) METHOD FOR PRODUCING 2-AMINO-SUBSTITUTED BENZALDEHYDE COMPOUND

(71) Applicant: Nippon Soda Co., Ltd., Chiyoda-ku, Tokyo (JP)

(72) Inventor: Shinichi Kobayashi, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/504,499

(22) PCT Filed: Aug. 25, 2015

(86) PCT No.: PCT/JP2015/073836
§ 371 (c)(1),
(2) Date: Feb. 16, 2017

(87) PCT Pub. No.: WO2016/035609
PCT Pub. Date: Mar. 10, 2016

(65) Prior Publication Data
US 2017/0226046 A1    Aug. 10, 2017

(30) Foreign Application Priority Data

Sep. 1, 2014 (JP) .................................. 2014-177563

(51) Int. Cl.
| C07C 223/06 | (2006.01) |
| C07C 221/00 | (2006.01) |
| C07D 317/16 | (2006.01) |
| C07D 317/28 | (2006.01) |

(52) U.S. Cl.
CPC .......... *C07C 223/06* (2013.01); *C07C 221/00* (2013.01); *C07D 317/16* (2013.01); *C07D 317/28* (2013.01)

(58) Field of Classification Search
None
See application file for complete search history.

(56) References Cited

U.S. PATENT DOCUMENTS

2002/0137741 A1    9/2002    Desconclois et al.

FOREIGN PATENT DOCUMENTS

| CN | 103030568 A | 4/2013 |
| DE | 2306919 A1 | 8/1974 |
| JP | 05-255211 A | 10/1993 |
| JP | 08-283217 A | 10/1996 |
| JP | 2000-007627 A | 1/2000 |
| JP | 2003-503495 A | 1/2003 |
| JP | 2013-237648 A | 11/2013 |
| WO | WO 2007/117607 A2 | 10/2007 |

OTHER PUBLICATIONS

Li et al., "An Improved Protocol for the Preparation of 3-Pyridyl- and Some Arylboronic Acids," J. Org. Chem., 2002, 67:5394-5397.
Zanirato, Paolo, "Synthesis, reactivity, and electronic structure of multifarious, five-membered heteroaryl and heteroaroyl azides," Arkivoc, 2009, 97-128.
Supplementary European Search Report dated Jan. 4, 2018, in EP 15837423.1.
Corpet et al., "Recent Advances in Electrophilic Amination Reactions," Synthesis, 2014, 46(17):2258-2271.
Takeuchi et al., "Direct Aromatic Amination by Azides : Reactions of Hydrazoic Acid and Butyl Azides with Aromatic Compounds in the Presence of Both Trifluoromethanesulfonic Acid and Trifluoroacetic Acid," Chem. Soc. Perkin Trans., 1993, 1(7):867-870.
International Search Report dated Nov. 17, 2015, in PCT/JP2015/073836.
CAS Registry No. 1598290-52-8, May 6, 2014 (retrieval date: Nov. 6, 2015), 1 page.
CAS Registry No. 1602097-79-9, May 11, 2014 (retrieval date: Nov. 6, 2015), 1 page.
CAS Registry No. 1026338-21-5, Jun. 8, 2008 (retrieval date: Nov. 6, 2015), 1 page.
CAS Registry No. 1602359-03-4, May 11, 2014 (retrieval date: Nov. 6, 2015), 1 page.

*Primary Examiner* — Clinton A Brooks
(74) *Attorney, Agent, or Firm* — Foley & Lardner LLP

(57) ABSTRACT

The present invention provides a method for producing a benzaldehyde in which an amino group is bonded in the 2 position, a halogeno group or an alkoxy group is bonded in the 3 position, and a hydrogen atom, an alkyl group, a halogeno group, an alkoxy group, or a cyano group is bonded independently in each of the 4, 5, and 6 positions, the method including: preparing a benzaldehyde in which a halogeno group or an alkoxy group is bonded in the 3 position, a hydrogen atom is bonded in the 2 position, and a hydrogen atom, an alkyl group, a halogeno group, an alkoxy group, or a cyano group is bonded independently in each of the 4, 5, and 6 positions so that a lithiation reaction is most active at the 2 position; acetal-protecting a formyl group in the benzaldehyde; sequentially performing lithiation, azidation, and amination of the 2 position; and the performing acetal deportection.

4 Claims, No Drawings

METHOD FOR PRODUCING 2-AMINO-SUBSTITUTED BENZALDEHYDE COMPOUND

TECHNICAL FIELD

The present invention relates to a method for producing a 2-amino-substituted benzaldehyde compound.

CROSS-REFERENCE TO RELATED APPLICATIONS

The present invention is a National Stage application PCT/JP2015/073836, filed Aug. 25, 2015, which claims priority on the basis of Japanese Patent Application No. 2014-177563 filed in Japan on Sep. 1, 2014, the contents of which are incorporated herein by reference.

BACKGROUND OF THE INVENTION

Amino benzaldehyde compounds are useful as agrochemical/pharmaceutical intermediates as disclosed in Patent Document 3 or Patent Document 4. Various methods for producing amino benzaldehyde compounds have been proposed.

For example, Patent Document 1 discloses a method for producing a 2-amino benzaldehyde compound by reacting triazanonane with an acid (see formulae (1)).

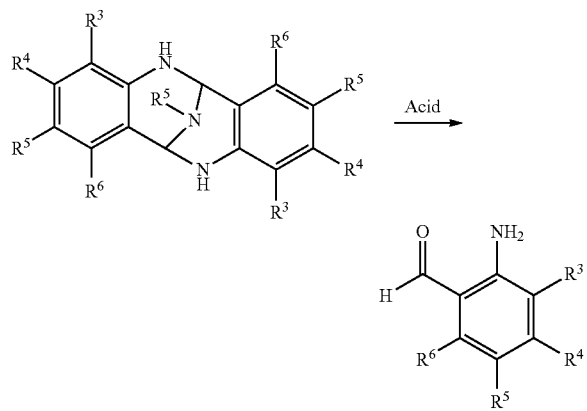

Patent Document 2 discloses a 3-fluoro-4-chloro-6-aminobenzaldehyde. The compound is obtained by conducting contact hydrogen reduction of 3-fluoro-4-chloro-6-nitrobenzaldehyde using a platinum-containing catalyst or a ruthenium-containing catalyst in an organic solvent under increased pressure. Patent Document 3 discloses 2-amino-3-methoxybenzaldehyde derivatives.

DOCUMENTS OF RELATED ART

Patent Documents

Patent Document 1: Japanese Unexample Patent Application, First Publication No. Hei 5-255211
Patent Document 2: Japanese Unexample Patent Application, First Publication No. Hei 8-283217
Patent Document 3: WO 2007/117607 A1
Patent Document 4: Japanese Laid-Open Patent Application No. 2013-237648

SUMMARY OF THE INVENTION

Problems to be Solved by the Invention

A 2-amino-3-halogeno-benzaldehyde or a 2-amino-3-alkoxy-benzaldehyde is a compound having an unstable structure in which a formyl group, an amino group, and either a halogeno group or an alkoxy group are substituted adjacently in a benzene ring. Condensation easily occurs between molecules in the compound. Accordingly, it is difficult to obtain a 2-amino-3-halogeno-benzaldehyde or a 2-amino-3-alkoxy-benzaldehyde under mild conditions in high yield.

An object of the present invention is to provide a method for producing a 2-amino-substituted benzaldehyde compound (see formula (III)) under mild conditions in high yield.

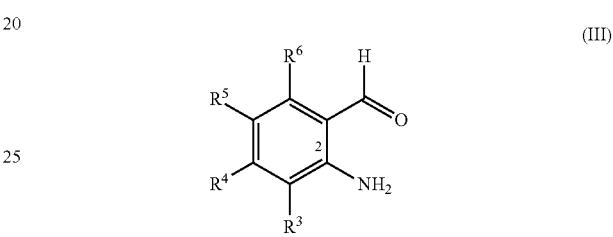

(III)

In the formula (III), $R^3$ represents a halogeno group or an alkoxy group. $R^4$, $R^5$, and $R^6$ each independently represent a hydrogen atom, an alkyl group, a halogeno group, an alkoxy group, or a cyano group.

Means to Solve the Problems

Studies have been conducted in order to solve the above-described problems, and as a result, the present invention including the following aspects have been completed.

(1) A method for producing a benzaldehyde in which an amino group is bonded in a 2 position, a halogeno group or an alkoxy group is bonded in a 3 position, and a hydrogen atom, an alkyl group, a halogeno group, an alkoxy group, or a cyano group is bonded independently in each of 4, 5, and 6 positions, the method containing:

preparing a benzaldehyde in which the halogeno group or the alkoxy group is bonded in the 3 position, a hydrogen atom is bonded in the 2 position, and the hydrogen atom, the alkyl group, the halogeno group, the alkoxy group, or the cyano group is bonded independently in each of the 4, 5, and 6 positions so that a lithiation reaction is most active at the 2 position (hereinafter, abbreviated as 2-unsubstituted benzaldehyde (I-1));

acetal-protecting a formyl group in the 2-unsubstituted benzaldehyde (I-1);

sequentially performing lithiation, azidation, and amination of the 2 position; and subsequently performing acetal deportection.

(2) A method for producing a benzaldehyde in which an amino group is bonded in a 2 position, a halogeno group or an alkoxy group is bonded in a 3 position, and a hydrogen atom, an alkyl group, a halogeno group, an alkoxy group, or a cyano group is bonded independently in each of 4, 5, and 6 positions, the method containing:

preparing a benzaldehyde in which the halogeno group or the alkoxy group is bonded in the 3 position, a hydrogen atom is bonded in the 2 position, and the hydrogen atom, the alkyl group, the halogeno group, the alkoxy group, or the cyano group is bonded independently in each of the 4, 5, and 6 positions so that a boration reaction is most active at the 2 position (hereinafter, abbreviated as 2-unsubstituted benzaldehyde (I-2));

acetal-protecting a formyl group in the 2-unsubstituted benzaldehyde (I-2);

sequentially performing boration, azidation, and amination of the 2 position; and subsequently performing acetal deportection.

(3) The method according to (1) or (2), wherein the 2-unsubstituted benzaldehyde (I-1) or (I-2) is a compound of formula (I-12):

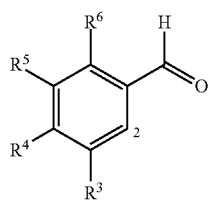

(in the formula (I-12), $R^3$ represents a halogeno group or an alkoxy group, $R^4$, $R^5$, and $R^6$ each independently represent a hydrogen atom, an alkyl group, a halogeno group, an alkoxy group, or a cyano group, wherein in a case where $R^4$ is a hydrogen atom, $R^5$ is a hydrogen atom, an alkyl group, or a cyano group, in a case where $R^5$ is a hydrogen atom, at least one of $R^4$ and $R^6$ is a hydrogen atom, an alkyl group, or a cyano group, and in a case where $R^6$ is a hydrogen atom, $R^5$ is a hydrogen atom, an alkyl group, or a cyano group).

(4) A compound of formula (III-1):

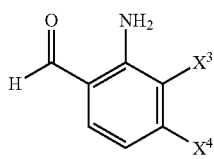

in the formula (III-1), $X^3$ and $X^4$ each independently represent a halogeno group.

Effects of the Invention

The 2-amino-3, 4-dihalobenzaldehyde (see formula (III-1)) according to the present invention is a novel compound. The 2-amino-3,4-dihalobenzaldehyde according to the present invention is useful as an agrochemical/pharmaceutical intermediate. The production method according to the present invention makes it possible to obtain a 2-amino-substituted benzaldehyde compound (see formula (III)) useful as an agrochemical/pharmaceutical intermediate, such as a 2-amino-3,4-dihalobenzaldehyde, in high yield.

EMBODIMENTS FOR CARRYING OUT THE INVENTION

A 2-amino-substituted benzaldehyde compound obtained in accordance with a production method according to the present invention is a benzaldehyde in which an amino group is bonded in a 2 position, a halogeno group or an alkoxy group is bonded in a 3 position, and a hydrogen atom, an alkyl group, a halogeno group, an alkoxy group, or a cyano group is bonded independently in each of 4, 5, and 6 positions. The 2-amino-substituted benzaldehyde compound is a compound of formula (III).

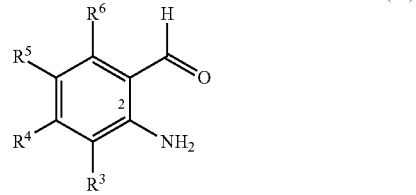

In the formula (III), $R^3$ represents a halogeno group or an alkoxy group. $R^4$, $R^5$, and $R^6$ each independently represent a hydrogen atom, an alkyl group, a halogeno group, an alkoxy group, or a cyano group.

Among the compounds of formula (III), a compound of formula (III-1) is a novel compound.

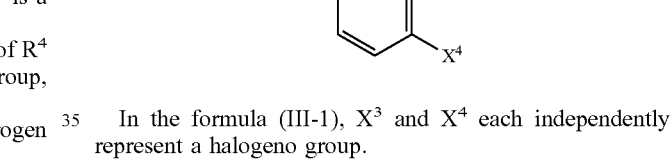

In the formula (III-1), $X^3$ and $X^4$ each independently represent a halogeno group.

The compound of formula (III) is useful as an agrochemical/pharmaceutical intermediate.

(First Aspect)

The method for producing a 2-amino-substituted benzaldehyde compound according to the first aspect of the present invention is a method containing: preparing a 2-unsubstituted benzaldehyde (I-1), acetal-protecting a formyl group in the 2-unsubstituted benzaldehyde (I-1), sequentially performing lithiation, azidation, and amination of the 2 position, and subsequently performing acetal deportection.

The 2-unsubstituted benzaldehyde (I-1) available in the present invention is a benzaldehyde in which a halogeno group or an alkoxy group is bonded in the 3 position, a hydrogen atom is bonded in the 2 position, and a hydrogen atom, an alkyl group, a halogeno group, an alkoxy group, or a cyano group is bonded independently in each of the 4, 5, and 6 positions so that lithiation reaction is most active at the 2 position. Specifically, the 2-unsubstituted benzaldehyde (I-1) is a compound of formula (I-1).

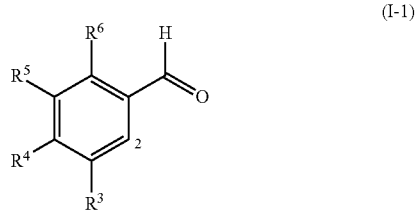

In the formula (I-1), $R^3$ represents a halogeno group or an alkoxy group, and $R^4$, $R^5$, and $R^6$ each independently represent a hydrogen atom, an alkyl group, a halogeno group, an alkoxy group, or a cyano group.

The 2-unsubstituted benzaldehyde (I-1) preferably available in the present invention is a compound of formula (I-12).

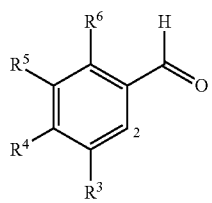

(In the formula (I-12), $R^3$ represents a halogeno group or an alkoxy group, and $R^4$, $R^5$, and $R^6$ each independently represent a hydrogen atom, an alkyl group, a halogeno group, an alkoxy group, or a cyano group, provided that in the case where $R^4$ is a hydrogen atom, $R^5$ is a hydrogen atom, an alkyl group, or a cyano group, in the case where $R^5$ is a hydrogen atom, at least one of $R^4$ and $R^6$ is a hydrogen atom, an alkyl group, or a cyano group, and in the case where $R^6$ is a hydrogen atom, $R^5$ is a hydrogen atom, an alkyl group, or a cyano group.)

The 2-unsubstituted benzaldehyde (I-1) may be obtained, for example, by performing chloromethylation of a benzene in which a halogeno group or an alkoxy group is bonded in the 3 position, a hydrogen atom is bonded in the 2 position, and a hydrogen atom, an alkyl group, a halogeno group, an alkoxy group, or a cyano group is bonded independently in each of the 4, 5, and 6 positions so that lithiation reaction is most active at the 2 position using a conventional method, and then oxidizing the resultant (see formulae (A)).

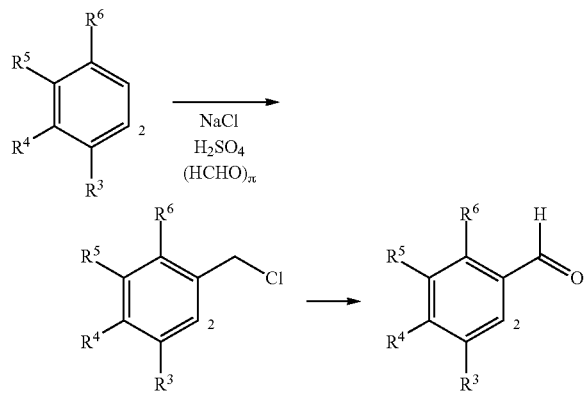

The process of acetal-protecting a formyl group in the 2-unsubstituted benzaldehyde (I-1) may be performed using a conventional method. Examples thereof include a method in which a diol is reacted under acidic conditions. As the diol, a 1,2-diol such as ethylene glycol, or a 1,3-diol such as 1,3-propanediol is preferably used. Alternatively, a monovalent alcohol having 1 to 6 carbon atoms is preferably used. Among the monovalent alcohol having 1 to 6 carbon atoms, a monovalent alcohol having 1 to 3 carbon atoms is more preferably used, and methanol or ethanol is even more preferably used. The reaction is often used to protect a carbonyl group. Since the reaction is a reversible reaction, it is preferable to use the diol or the monovalent alcohol excessively or remove by-product water to complete the reaction.

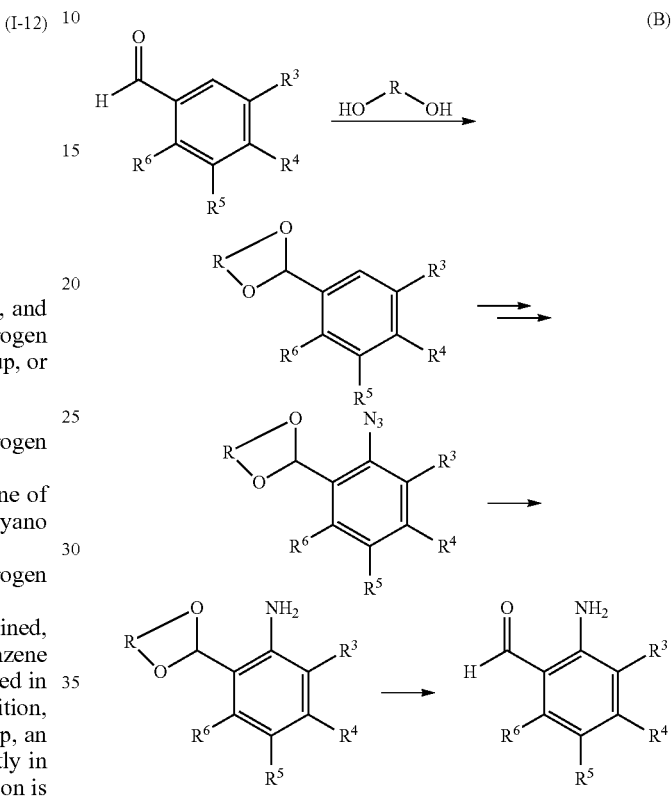

The processes of lithiation, azidation, and amination of the 2 position and acetal deportection may be performed using conventional methods. The process of lithiation may be performed by the action of an organolithium compound such as n-butyllithium, for example. The process of azidation may be performed by the action of an azide compound such as tosyl azide, for example. The process of amination may be performed, for example, by conducting reduction reaction in the presence of a palladium catalyst. The process of acetal deportection may be performed, for example, by conducting water-addition.

Examples of the production method according to the first aspect of the present invention include a method containing: reacting a 3,4-disubstituted benzaldehyde with a diol to obtain a 3,4-disubstituted phenyl-cyclic acetal, subjecting the 3,4-disubstituted phenyl-cyclic acetal to lithiation, reacting the resultant with an azidation agent to obtain a (2-azido-3,4-disubstituted phenyl)-cyclic acetal, reducing the (2-azido-3,4-disubstituted phenyl)-cyclic acetal to obtain a (2-amino-3,4-disubstituted phenyl)-cyclic acetal, and then removing the diol from the (2-amino-3,4-disubstituted phenyl)-cyclic acetal (see formulae (C)).

In the formulae (C), $R^3$ and $R^4$ are substituents. It is preferable that the substituents be inactive or low-active against the diols, azide, or reductant. As the substituent, a halogeno group is preferable, and a fluoro group is more preferable.

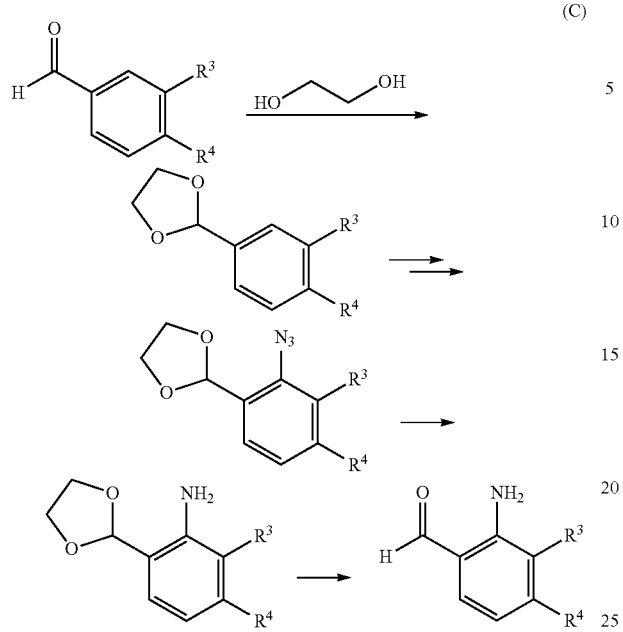

(C)

As the 3,4-disubstituted benzaldehyde, a commercially-available one or one that may be produced using a conventional method by those skilled in the art may be used. For example, a 3,4-difluorobenzaldehyde may be obtained by making hydrogen peroxide act on 4-chloromethyl-1,2-difluorobenzene obtained by: reacting carbon monoxide with 4-bromo-1,2-difluorobenzene obtained by brominating 1,2-difluorobenzene; or making sodium salt, sulfuric acid, and paraformaldehyde act on 1,2-difluorobenzene.

It is preferable that the 3,4-disubstituted benzaldehyde be reacted with a diol under acidic conditions. As the diol, a 1,2-diol such as ethylene glycol, or a 1,3-diol such as 1,3-propanediol is preferably used. The reaction is often used to protect a carbonyl group. Since the reaction is a reversible reaction, it is preferable to use the diol excessively or remove by-product water to complete the reaction.

Then, the 2 position lithiated by the action of a base such as n-BuLi. Then, an azido group is introduced into a benzene ring by nucleophilic substitution induced by an azidation agent such as toluenesulfonyl azide, or trifluoromethanesulfonyl azide. An azido group is preferentially introduced in the 2 position.

The azido group may be made to be an amino group by making a hydrogen gas act on (2-azido-3,4-disubstituted phenyl)-cyclic acetal in the presence of palladium catalyst, or making a reductant such as lithium aluminum hydride or a phosphorus compound act thereon.

Then, the diol is eliminated from the cyclic acetal structure serving as a protective group to bring back to a carbonyl group. The reaction may be conducted in the presence of water under acidic conditions.

(Second Aspect)

A method for producing a 2-amino-substituted benzaldehyde compound according to the second aspect of the present invention includes: preparing a 2-unsubstituted benzaldehyde (I-2), acetal-protecting a formyl group in the 2-unsubstituted benzaldehyde (I-2), sequentially performing boration, azidation, and amination of the 2 position, and subsequently performing acetal deportection.

The 2-unsubstituted benzaldehyde (I-2) available in the present invention is a benzaldehyde in which a halogeno group or an alkoxy group is bonded in the 3 position, a hydrogen atom is bonded in the 2 position, and a hydrogen atom, an alkyl group, a halogeno group, an alkoxy group, or a cyano group is bonded independently in each of the 4, 5, and 6 positions so that boration reaction is most active at the 2 position. Specifically, the compound is a compound of formula (I-2).

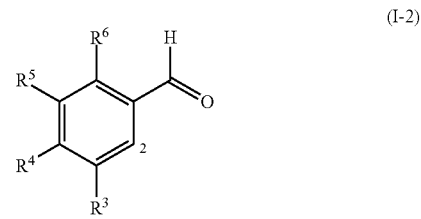

(I-2)

In the formula (I-2), $R^3$ represents a halogeno group or an alkoxy group. $R^4$, $R^5$, and $R^6$ each independently represent a hydrogen atom, an alkyl group, a halogeno group, an alkoxy group, or a cyano group. The 2-unsubstituted benzaldehyde (I-2) preferably used in the present invention is a compound of formula (I-12). The 2-unsubstituted benzaldehyde (I-2) may be produced using the same method as that used to produce the 2-unsubstituted benzaldehyde (I-1).

The process of acetal-protecting a formyl group in the 2-unsubstituted benzaldehyde (I-2) may be conducted using the same method as that mentioned in the first aspect.

The processes of boration, azidation, and amination of the 2 position, and acetal deportection may be conducted using conventional methods. The process of boration may be conducted by the action of a borate reactant, for example. The process of azidation may be conducted by the action of an azide compound such as tosyl azide, for example. The process of amination may be conducted by reduction reaction in the presence of palladium catalyst. The process of acetal deportection may be conducted by water-addition, for example.

Examples of the production method according to the second aspect of the present invention include a method containing: reacting a 3,4-disubstituted benzaldehyde with a diol to obtain a 3,4-disubstituted phenyl-cyclic acetal; making a borate reactant act on the 3,4-disubstituted phenyl-cyclic acetal to obtain a (2-dihydroxyboryl-3,4-disubstituted phenyl)-cyclic acetal; reacting the (2-dihydroxyboryl-3,4-disubstituted phenyl)-cyclic acetal with an azidation agent and then reducing the resultant to obtain a (2-amino-3,4-disubstituted phenyl)-cyclic acetal; and then eliminating a diol from the (2-amino-3,4-disubstituted phenyl)-cyclic acetal. It is preferable that substituents at the 3 position or the 4 position be inactive or low-active against the diol, borate agent, azidation agent, and reductant. As the substituents, a halogeno group is preferable, and a fluoro group is more preferable.

The production method according to the second aspect is different from that of the first aspect in terms that the 3,4-disubstituted phenyl-cyclic acetal is borated instead of lithiated. The borate reactant is a material composed of an organolithium such as n-BuLi and trialkoxy borane. The reaction produces a (2-dihydroxyboryl-3,4-disubstituted phenyl)-cyclic acetal.

An azide and a reductant such as $NaBH_4$ are made to act on the produced (2-dihydroxyboryl-3,4-disubstituted phenyl)-cyclic acetal in the presence of a copper catalyst to progress the conversion and deprotection into an amino group.

The above-mentioned reactions proceed under mild conditions, and condensation reaction between molecules hardly occurs. The method according to the present invention makes it possible to obtain compounds of formula (III) such as a 2-amino-3,4-disubstituted benzaldehyde in high yield.

EXAMPLES

The present invention will be explained in more detail by showing examples. However, the technical scope of the present invention is not limited to the examples.

Example 1 Production of 2-amino-3,4-difluorobenzaldehyde (Step 1) Production of 2-(3,4-difluorophenyl)-1,3-dioxolane

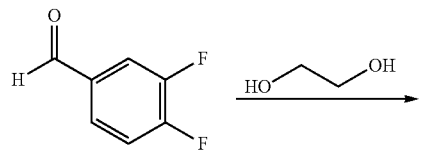

50.22 g of 3,4-difluorobenzaldehyde (purity 99.7%, 352 mmol) was dissolved in 176 mL of toluene. 23 mL (389 mmol) of ethylene glycol was added to the solution. The reaction system was purged with nitrogen, and refluxed for 2.4 hours while dehydrating using a Dean-Stark apparatus. Thereafter, the reaction liquid was cooled to 94° C., 0.33 g (1.73 mmol) of p-toluenesulfonic acid monohydrate was added thereto, and then the mixture was refluxed for 1.7 hours. 4.2 mL (71.0 mmol) of ethylene glycol was further added to the resultant, and the mixture was refluxed for 2.5 hours. The reaction liquid was cooled to room temperature. 100 mL of 5% aqueous solution of sodium hydroxide was added to the resultant. The aqueous phase was separated, the product was extracted with 50 mL of toluene, the organic phase was corrected, and then washed with 50 mL of water. Then, the resultant was washed with 50 mL of saturated saline, dried with magnesium sulfate, and filtered. As a result of the analysis of the filtrate by HPLC, the yield of 2-(3,4-difluorophenyl)-1,3-dioxolane was 94.1%.

The result of $^1$H-NMR analysis of the obtained compound was shown below.

$^1$H-NMR (400 MHz, CDCl$_3$) δ 7.33-7.12 (m, 3H), 5.75 (s, 1H), 4.12-4.00 (m, 4H).

(Step 2) Production of 2-(2-azido-3,4-difluorophenyl)-1,3-dioxolane

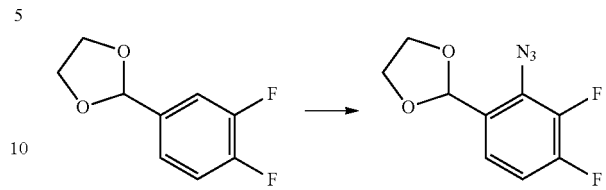

(Batch Reaction)

1.93 g of 2-(3,4-difluorophenyl)-1,3-dioxolane (purity 96.1%, 9.96 mmol) was dissolved in 20 mL of toluene under a nitrogen stream. The reaction liquid was cooled to −78° C. 1.65 mL (11.1 mmol) of N,N,N',N'-tetramethylethylenediamine was added to the resultant, and then 6.9 mL (11.0 mmol) of 1.6M hexane solution of n-butyllithium was added dropwise over 8 minutes. The resultant was stirred for 1 hour at −78° C.

Thereafter, 22.5 mL (15.2 mmol) of 15% toluene solution of tosyl azide was added dropwise over 5 minutes, and then the reaction solution was warmed to 0° C. and then stirred for 1 hour. 50 mL of water was added thereto, and the toluene phase was separated. The product was extracted from the toluene phase with 20 mL of water. The aqueous phase was corrected, and extracted four times with 20 mL of ethyl acetate. The ethyl acetate phase was corrected and combined, washed with 20 mL of saturated saline, dried with magnesium sulfate, and then filtered. As a result of the analysis of the filtrate by HPLC, the yield of 2-(2-azido-3,4-difluorophenyl)-1,3-dioxolane was 83.7%.

(Step 3) Production of 6-(1,3-dioxolan-2-yl)-2,3-difluoroaniline

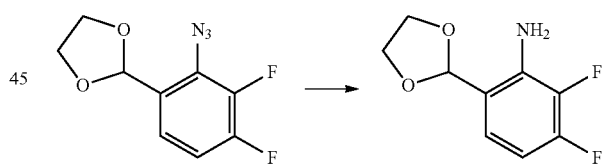

22.3 mg of 10% palladium carbon (moisture 55.24%, palladium pure content 9.3 μmol) was added to 11.30 g (10.0 mmol) of 20.2% ethyl acetate solution of 2-(2-azido-3,4-difluorophenyl)-1,3-dioxolan. The inside of the system was replaced with nitrogen, and then replaced with hydrogen. Thereafter, the reaction solution was heated to 40° C., and then stirred for 3 hours. The reaction solution was cooled to room temperature, the inside of the system was replaced with nitrogen, the catalyst was filtered off, and then the resultant was washed with ethyl acetate. As a result of the quantitative analysis of the filtrate, the yield of 6-(1,3-dioxolan-2-yl)-2,3-difluoroaniline was 95.5%.

The result of $^1$H-NMR analysis of the obtained compound was shown below.

$^1$H-NMR (400 MHz, CDCl$_3$) δ 7.03-6.99 (m, 1H), 6.53-6.47 (m, 1H), 5.78 (s, 1H), 4.40 (br, 2H), 4.13-4.03 (m, 4H).

(Step 4) Production of
2-amino-3,4-difluorobenzaldehyde

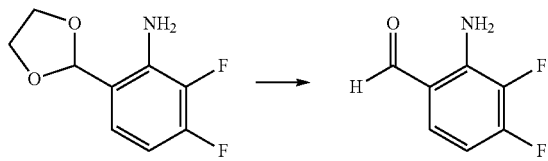 [SMILES: Nc1c(C2OCCO2)ccc(F)c1F ; Nc1c(C=O)ccc(F)c1F]

1.01 g of 6-(1,3-dioxolan-2-yl)-2,3-difluoroaniline (purity 99.5%, 5.00 mmol) was dissolved in 15 mL of a mixture composed of acetone and water at a ratio of 1:1. The reaction solution was heated to 30° C., 14.7 mg (0.0584 mmol) of pyridinium p-toluenesulfonate was added thereto, and the mixture was stirred for 2.7 hours. Thereafter, the reaction solution was heated to 40° C. and then stirred for 2 hours. The reaction liquid was cooled to room temperature, left still over night, and then acetone was added thereto to obtain a homogeneous solution. As a result of the quantitative analysis of the solution, the yield of 2-amino-3,4-difluorobenzaldehyde was 96.5%.

The result of $^1$H-NMR analysis of the obtained compound was shown below.

$^1$H-NMR (400 MHz, CDCl$_3$) δ 9.82 (d, J=1.6 Hz, 1H), 7.30-7.26 (m, 1H), 6.58-6.52 (m, 1H), 6.30 (br, 2H).

Example 2 Production of 2-amino-3,
4-difluorobenzaldehyde 2-amino-3, 4-difluorobenzaldehyde was produced in the same manner as in Example 1, except that Step 2 was carried out in a flow reaction mentioned below.
(Flow Reaction)
4.14 g of 2-(3, 4-difluorophenyl)-1, 3-dioxolane (purity 96.0%, 21.2 mmol) and 2.72 g (23.4 mmol) of N,N,N',N'-tetramethylethylenediamine were weighted in a 50 mL measuring flask, and diluted with toluene to 50 mL total to obtain a solution (referred to as liquid A).

The liquid A and a 1.6 M hexane solution of n-butyllithium (referred to as liquid B) were sucked using 50 mL gas tight syringes, respectively, and set to syringe pumps to connect to a flow reactor. The flow rates of the pumps were set so that the retention time of the mixture liquid was 30 seconds and the amount of n-butyllithium relative to the substrate was 1.1 equivalents. A pre-cooling portion and a lithiation retention portion of the flow reactor was cooled to −30° C., and transfer of the liquid A and the liquid B was started at the same time. The transfer process was continued until the mixture liquid of the liquid A and liquid B flowed out, and then the transfer process was stopped once. A reaction container containing 22.5 mL (15.2 mmol) of 15% toluene solution of tosyl azide was cooled to 0° C. under a nitrogen stream, and then connected to the flow reactor to restart transfer of the liquids. Transfer of both the liquid A and the liquid B was stopped when transfer of 23.54 mL (substrate 10.0 mmol) of the liquid A was completed. The total amount of the sent liquid B was 6.883 mL (n-butyllithium 11.0 mmol).

Thereafter, the resultant was stirred at 0° C. for 1 hour. 50 mL of water was added thereto, the toluene phase was separated, and the product was extracted with 20 mL of water. The aqueous phase was corrected, and extracted four times with 20 mL of ethyl acetate. The ethyl acetate phase was corrected and combined, washed with 20 mL of saturated saline, dried with magnesium sulfate, and then filtered. As a result of the analysis of the filtrate by HPLC, the yield of 2-(2-azido-3,4-difluorophenyl)-1,3-dioxolane was 94.1%.

The result of $^1$H-NMR analysis of the obtained compound was shown below.

$^1$H-NMR (400 MHz, CDCl$_3$) δ 7.30 (ddd, J=8.8, 6.0, 2.4 Hz, 1H), 6.95 (dt, J=8.8, 7.2 Hz, 1H), 5.96 (s, 1H), 4.15-4.02 (m, 4H).

INDUSTRIAL APPLICABILITY

The production method according to the present invention makes it possible to obtain a 2-amino-substituted benzaldehyde compound useful as an agrochemical/pharmaceutical intermediate, such as 2-amino-3,4-dihalobenzaldehyde, in high yield. Accordingly, the present invention is extremely useful in industrially.

The invention claimed is:

1. A method for producing a benzaldehyde in which an amino group is bonded in a 2 position, a halogeno group or an alkoxy group is bonded in a 3 position, and a hydrogen atom, an alkyl group, a halogeno group, an alkoxy group, or a cyano group is bonded independently in each of 4, 5, and 6 positions, the method comprising:

preparing a benzaldehyde in which the halogeno group or the alkoxy group is bonded in the 3 position, a hydrogen atom is bonded in the 2 position, and the hydrogen atom, the alkyl group, the halogeno group, the alkoxy group, or the cyano group is bonded independently in each of the 4, 5, and 6 positions so that a lithiation reaction is most active at the 2 position (hereinafter, abbreviated as 2-unsubstituted benzaldehyde (I-1));

acetal-protecting a formyl group in the 2-unsubstituted benzaldehyde (I-1);

sequentially performing lithiation, azidation, and amination of the 2 position; and subsequently performing acetal deportection.

2. A method for producing a benzaldehyde in which an amino group is bonded in a 2 position, a halogeno group or an alkoxy group is bonded in a 3 position, and a hydrogen atom, an alkyl group, a halogeno group, an alkoxy group, or a cyano group is bonded independently in each of 4, 5, and 6 positions, the method comprising:

preparing a benzaldehyde in which the halogeno group or the alkoxy group is bonded in the 3 position, a hydrogen atom is bonded in the 2 position, and the hydrogen atom, the alkyl group, the halogeno group, the alkoxy group, or the cyano group is bonded independently in each of the 4, 5, and 6 positions so that a boration reaction is most active at the 2 position (hereinafter, abbreviated as 2-unsubstituted benzaldehyde (I-2));

acetal-protecting a formyl group in the 2-unsubstituted benzaldehyde (1-2);

sequentially performing boration, azidation, and amination of the 2 position; and subsequently performing acetal deportection.

3. The method according to claim 1, wherein the 2-unsubstituted benzaldehyde (I-1) or (I-2) is a compound of formula (I-12):

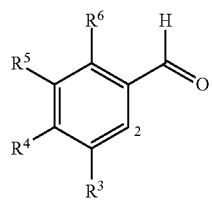

(I-12)

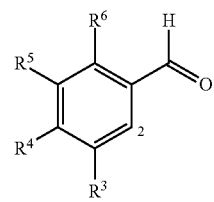

(I-12)

(in the formula (I-12),
R³ represents a halogeno group or an alkoxy group,
R⁴, R⁵, and R⁶ each independently represent a hydrogen atom, an alkyl group, a halogeno group, an alkoxy group, or a cyano group,
wherein in a case where R⁴ is a hydrogen atom, R⁵ is a hydrogen atom, an alkyl group, or a cyano group,
in a case where R⁵ is a hydrogen atom, at least one of R⁴ and R⁶ is a hydrogen atom, an alkyl group, or a cyano group, and
in a case where R⁶ is a hydrogen atom, R⁵ is a hydrogen atom, an alkyl group, or a cyano group).

4. The method according to claim 2, wherein the 2-unsubstituted benzaldehyde (I-1) or (I-2) is a compound of formula (I-12):

(in the formula (I-12),
R³ represents a halogeno group or an alkoxy group,
R⁴, R⁵, and R⁶ each independently represent a hydrogen atom, an alkyl group, a halogeno group, an alkoxy group, or a cyano group,
wherein in a case where R⁴ is a hydrogen atom, R⁵ is a hydrogen atom, an alkyl group, or a cyano group,
in a case where R⁵ is a hydrogen atom, at least one of R⁴ and R⁶ is a hydrogen atom, an alkyl group, or a cyano group, and
in a case where R⁶ is a hydrogen atom, R⁵ is a hydrogen atom, an alkyl group, or a cyano group).

\* \* \* \* \*